(12) United States Patent
Yassour et al.

(10) Patent No.: US 6,866,680 B2
(45) Date of Patent: Mar. 15, 2005

(54) IMPLANTABLE STROKE PREVENTING DEVICE

(75) Inventors: Yuval Yassour, Haifa (IL); Ofer Yodfat, Reut (IL); Ygael Grad, Tel-Aviv (IL); Moshe Rosenfeld, Beit Halevy (IL); Daniel Levin, Haifa (IL)

(73) Assignee: MindGuard Ltd., Caesarea (IL)

( * ) Notice: Subject to any disclaimer, the term of this patent is extended or adjusted under 35 U.S.C. 154(b) by 338 days.

(21) Appl. No.: 09/950,027

(22) Filed: Sep. 10, 2001

(65) Prior Publication Data

US 2002/0049491 A1 Apr. 25, 2002

Related U.S. Application Data

(63) Continuation of application No. PCT/IL00/00145, filed on Mar. 9, 2000.

(51) Int. Cl.[7] .................................................. A61F 2/06
(52) U.S. Cl. ...................................................... 623/1.15
(58) Field of Search ................................ 623/1.39, 1.2, 623/1.15–1.19, 1.23, 1.4; 606/191, 192, 194, 195, 198, 200

(56) References Cited

U.S. PATENT DOCUMENTS

| | | | | |
|---|---|---|---|---|
| 4,760,849 A | * | 8/1988 | Kropf | 606/191 |
| 6,258,115 B1 | * | 7/2001 | Dubrul | 606/200 |
| 6,312,463 B1 | * | 11/2001 | Rourke et al. | 623/1.39 |

FOREIGN PATENT DOCUMENTS

| | | |
|---|---|---|
| WO | WO 98/47477 | 10/1998 |
| WO | WO 98/58599 | 12/1998 |
| WO | WO 99/32050 | 1/1999 |

* cited by examiner

Primary Examiner—Vy Q Bui
(74) Attorney, Agent, or Firm—G. E. Ehrlich (1995) Ltd.

(57) ABSTRACT

An implantable device for positioning in the vicinity of the bifurcation of the common carotid artery (CCA) into the internal carotid artery (ICA) and the external carotid artery (ECA), comprises a deflecting element suitable to deflect the flow of embolic material flowing in the CCS toward the ICA, into the ECA, without filtering.

5 Claims, 5 Drawing Sheets

IMPLANTABLE STROKE PREVENTING DEVICE

This application is a continuation of PCT/IL00/00145 filed Mar. 9, 2000.

FIELD OF THE INVENTION

The present invention relates to implantable stroke treating devices, and more specifically is concerned with a device for reducing the risk of embolic material entering into the internal carotid artery of an individual and blood clots (collectively and interchangeably referred to as "embolic material").

BACKGROUND OF THE INVENTION

A major portion of blood supply to the brain hemispheres is by two arteries, referred to as common carotid arteries (CCA), each of which branches off, or bifurcates as the term is at times used, into a so-called internal carotid artery (ICA) and an external carotid artery (ECA). Blood to the brain stem is supplied by two vertebral arteries.

Cerebrovascular diseases are considered among the leading causes of mortality and morbidity in the modern age. Strokes denote an abrupt impairment of brain function caused by pathologic changes occurring in blood vessels. The main cause of strokes is insufficient blood flow to the brain (referred to as "an ischemic stroke") which are about 80% of stroke cases.

Ischemic strokes are caused by sudden occlusion of an artery supplying blood to the brain. Occlusion or partial occlusion (stenosis) are the result of diseases of the arterial wall. Arterial atherosclerosis is by far the most common arterial disorder, and when complicated by thrombosis or embolism it is the most frequent cause of cerebral ischemia and infarction, eventually causing the cerebral stroke.

Cardioembolism causes about 15%–20% of all strokes. Stroke caused by heart disease is primarily due to embolism of thrombotic material forming on the atrial or ventricular wall or the left heart valve. These thrombi then detach and embolize into the arterial circulation. Emboli large enough can occlude large arteries in the brain territory and cause strokes.

Cardiogenetic cerebral embolism is presumed to have occurred when cardiac arrhythmia or structural abnormalities are found or known to be present. The most common cause of cardioembolic stroke is nonrheumatic (non-valvular) arterial fibrillation (AF), myocardial infarction, prothetic valves, rheumatic heart disease (RHD) and ischemic cardiomyopathy.

Such disorders are currently treated in different ways such as by drug management, surgery (carotid endarterectomy) in case of occlusive disease, or carotid angioplasty and carotid stents.

While endarterectomy, angioplasty and carotid stenting are procedures targeting at reopening the occluded artery, they do not prevent progression of new plaque (restenosis). Furthermore, embolisms from the new forming plaque in the internal carotid artery (with or without a stent implanted therein) can occlude smaller arteries in the brain and cause strokes. Even more so, the above treatment methods do not prevent proximal embolic sources, i.e. embolus formed at remote sites heart and ascending aorta) to pass through the reopened stenosis in the carotid and occlude smaller arteries in the brain.

It will also be appreciated that endarterectomy is not suitable for intracarnial arteries or in the vertebrobasilar system since these arteries are positioned within unacceptable environment (brain tissue, bone tissue) or are too small in diameter.

Introducing filtering means into blood vessels, in particular into veins, has been known for some time. However, filtering devices known in the art are generally of a complex design, which renders such devices unsuitable for implantation with carotid arteries, and unsuitable for handling fine embolic material. However, when considering the possible cerebral effects of even fine embolic material occluding an artery supplying blood to the brain, the consequences may be fatal or may cause irreversible brain damage.

However, in light of the short period of time during which brain tissue can survive without blood supply, there is significant importance to providing suitable means for preventing even small embolic material from entering the internal carotid artery, so as to avoid brain damage.

A drawback of prior art filtering means is their tendency to become clogged. On the one hand, in order to provide efficient filtering means, the filter should be of fine mesh. On the other hand, a fine mesh has a higher tendency toward, and risk of occlusion.

It should also be noted that the flow ratio between the ICA and the ECA is about 4:1. This ratio also reflects the much higher risk of embolic material flowing into the ICA.

It is thus an object of the present invention to provide an implantable deflecting device suitable to be positioned within a blood vessel supplying blood to the brain, and further suitable to deflect embolic material that would have flown into the internal carotid artery, into the external carotid artery, thereby preventing the entry of said embolic material into the internal carotid artery, and thus preventing extracranial embolus to occlude small intercranial arteries in the brain.

It is another object of the invention to provide a method for preventing conditions associated with embolic material.

Other objects of the invention will become apparent as the description proceeds.

SUMMARY OF THE INVENTION

The present invention provides an implantable device for positioning in the vicinity of the bifurcation of the common carotid artery (CCA) into the internal carotid artery (ICA) and the external carotid artery (ECA), comprising a deflecting element suitable to deflect the flow of embolic material flowing in the CCA toward the ICA, into the ECA.

Thus, in one aspect, the invention provides an implantable deflecting device for implanting at the vicinity of bifurcation of the common carotid artery (CCA) into the internal carotid artery (ICA) and the external carotid artery (ECA); the device comprising an anchoring member engageable with inner walls of a carotid artery, and one or more deflecting members for deflecting flow of embolic material into the ECA, substantially without obstructing blood flow into the ICA.

The anchoring member and the deflecting member may be integral with one another or attached or coupled to one another. In the present specification the anchoring member and the deflecting member may be referred to also as anchoring portion and deflecting portion, respectively.

By a preferred embodiment, at least the anchoring member is a stent adapted for insertion via the vasculature of an individual. The implantable deflecting device in accordance with any of the embodiments of the present invention may be permanently implanted or may be removed after a period of time, depending on the course of treatment and the medical procedure.

The deflecting member may be positioned at any location that fulfills two conditions: firstly, it does not occlude the flow of blood into the ICA, and secondly, it causes a deflection of the flow of embolic material into the ECA.

The one or more deflecting member may be integrally formed with the anchoring member or may be attached or coupled thereto either during manufacture, or after implanting the anchoring member within the artery.

In accordance with one specific embodiment of the invention, the anchoring member comprises a tubular portion for anchorage within the CCA with said one or more deflecting member accommodated within said tubular portion. In accordance with this embodiment the deflecting member generates a flow vector deflecting flow of embolic material into the ECA.

By another specific embodiment the one or more deflecting member is adapted for generating a centrifugal flow pattern deflecting the embolic material into the ECA Preferably, in accordance with the latter embodiment, the one or more deflecting member has a hemodynamic wing-like shape.

Alternatively, the one or more deflecting member comprises an array of wires arranged so as to form a helical path. Such wires typically have an imaginary point of intersection which is offset with respect to a longitudinal axis of the common carotid artery.

By another aspect of the present invention there is provided an implantable deflecting device for implanting at the vicinity of bifurcation of the common carotid artery (CCA) into the internal carotid artery (ICA) and the external carotid artery (ECA); the device comprising an anchoring member engageable with inner walls of a carotid artery, and one or more deflecting members, wherein the one or more deflecting member is so positioned and sized so that embolic material encountering it is deflected to flow into the ECA.

In another aspect the invention is directed to an arterial stent suitable to be positioned in the vicinity of the bifurcation of the common carotid artery (CCA) into the internal carotid artery (ICA) and the external carotid artery (ECA), comprising a deflecting device.

The invention is further directed to an arterial stent suitable to be positioned in the vicinity of the bifurcation of the common carotid artery (CCA) into the internal carotid artery (ICA) and the external carotid artery (ECA), coupled to a deflecting device.

In a further aspect, the invention is directed to the prevention of the occurrence, or the recurrence, of cerebrovascular diseases, particularly of stroke, comprising preventing the flow of embolic material flowing in the CCA from accessing the ICA, by deflecting the flow of said embolic material into the ECA. Prevention of the cerebrovascular disease is achieved by implanting, permanently or temporarily, in the vicinity of the bifurcation of the common carotid artery (CCA) into the internal carotid artery (ICA) and the external carotid artery (ECA), a deflecting device according to the invention.

All the above and other characteristics and advantages of the invention will be better understood through the following illustrative and non-limitative detailed description of preferred embodiments thereof.

BRIEF DESCRIPTION OF THE DRAWINGS

In order to better understand the invention and to illustrate it in practice, non-limiting examples of some preferred embodiments will now be described, with reference to the accompanying drawings, in which.

DETAILED DESCRIPTION OF PREFERRED EMBODIMENTS

Figure 1:
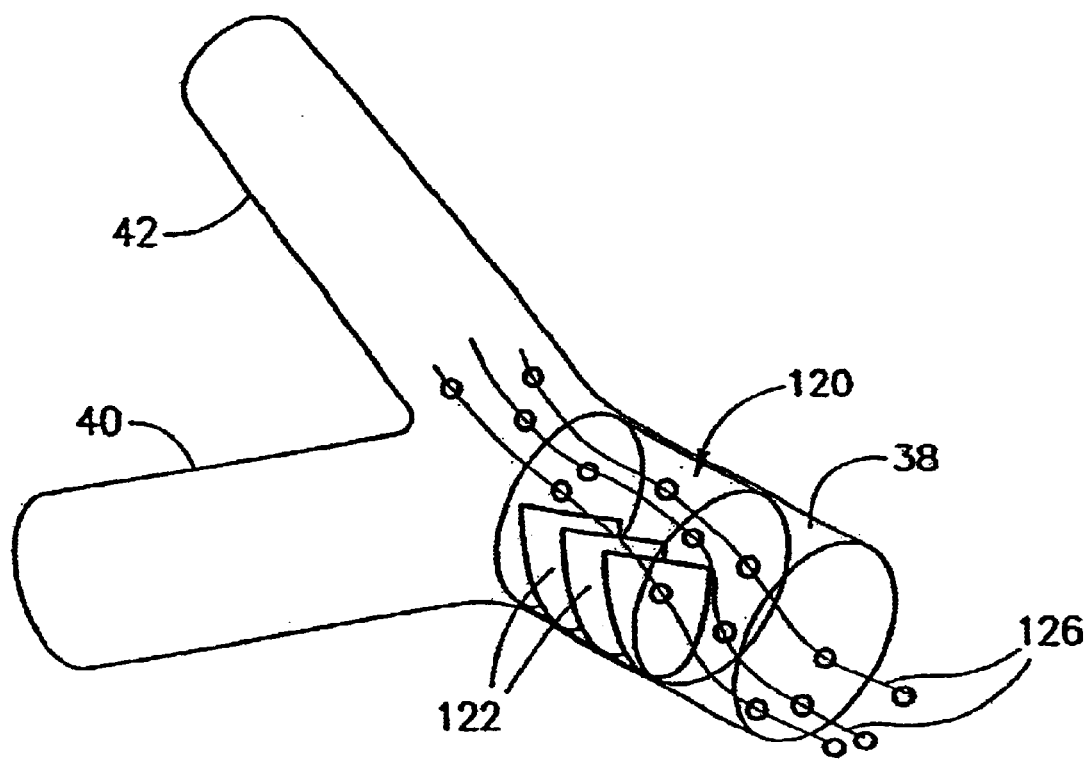
FIG. 1 is a schematic illustration of a deflecting device located within the common carotid artery and fitted with fluid flow diverting means.

Attention is first directed to FIG. 1, in which there is schematically illustrated a deflecting device generally designated 120, entirely positioned within the common carotid artery 38. The device 120 is fitted with three deflecting surfaces 122 (the number of deflecting surfaces and their design may vary depending on the desired hemodynamic parameters).

The arrangement is such that embolic material (represented by flow lines 126) flows via CCA 38, encounters deflecting surfaces 122 and rather than entering the ICA 40 is deflected into the ECA 42. As will be apparent to the skilled person, the flow lines of the embolic material are dictated by the arrangement of the deflecting surfaces 122, and can be calculated on the basis of the blood flow parameters. The deflecting elements are non-occluding, inasmuch as they allow the flow of some of the blood to proceed through openings provided therein, wherein the openings are delimited by wire-like or rod-like members of defined thickness.

A preferred embodiment of the device of FIG. 1 is shown in FIG. 2. The deflecting device 120 is provided with deflecting surfaces 122, the direction of blood flow being that of arrow f. The deflecting surfaces are seen in FIG. 2B to be, according to this particular embodiment of the invention, made of a wire mesh, which is enlarged in FIG. 2C and is seen to have a square side dimension "a", and a wire thickness "t". The holes in the wire mesh of deflecting surfaces 122 are significantly smaller than the holes 123 found elsewhere in the deflecting device 120.

Figure 2A:
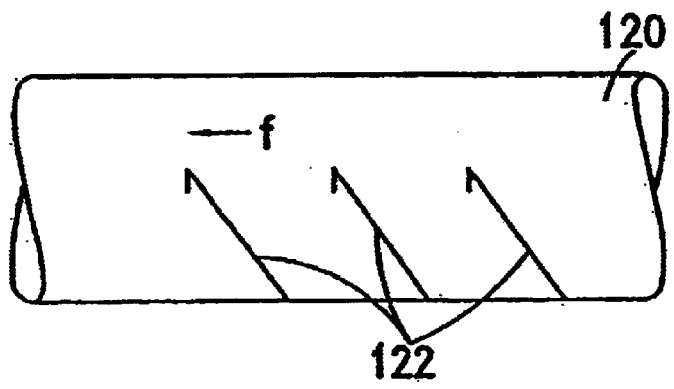
FIG. 2A is a schematic perspective transparent illustration of a deflecting device of FIG. 1, according to a preferred embodiment.
Figure 2B:
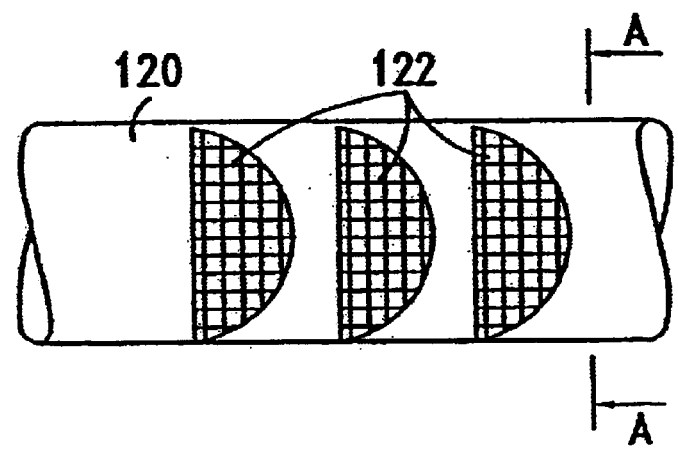
FIG. 2B is a schematic top view of the device of FIG. 2A.
Figure 2C:
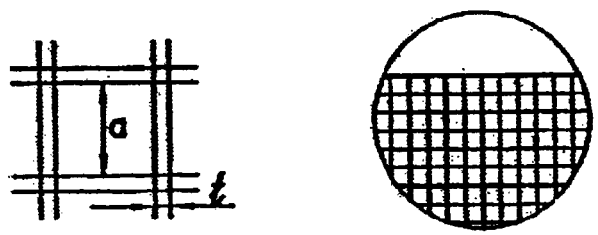
FIG. 2C shows the mesh-like deflecting device of FIG. 2B in cross-sectional view taken along the A—A axis.
Figure 2D:
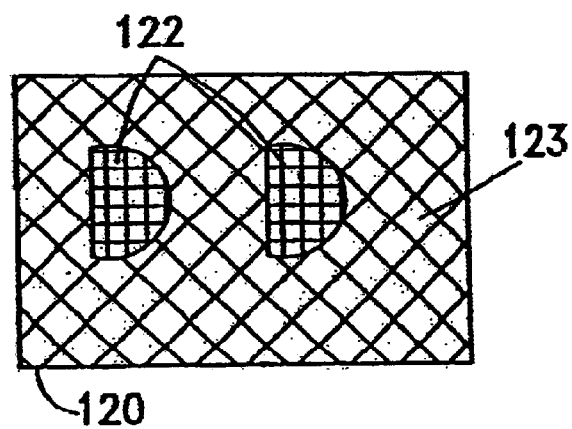
FIG. 2D is a schematic unfolded view of the device of FIG. 2A during delivery.

Delivery of the device is facilitated, as shown in FIG. 2D, if when the stent-like device is in collapsed form, the deflecting surfaces are essentially parallel to its surface. Expansion of the stent-like device leads to the raising of the deflecting surfaces and to their positioning illustrated in FIG. 2A This arrangement can be easily devise by the skilled person, and is therefore not disclosed herein in detail, for the sake of brevity.

Figure 3A:
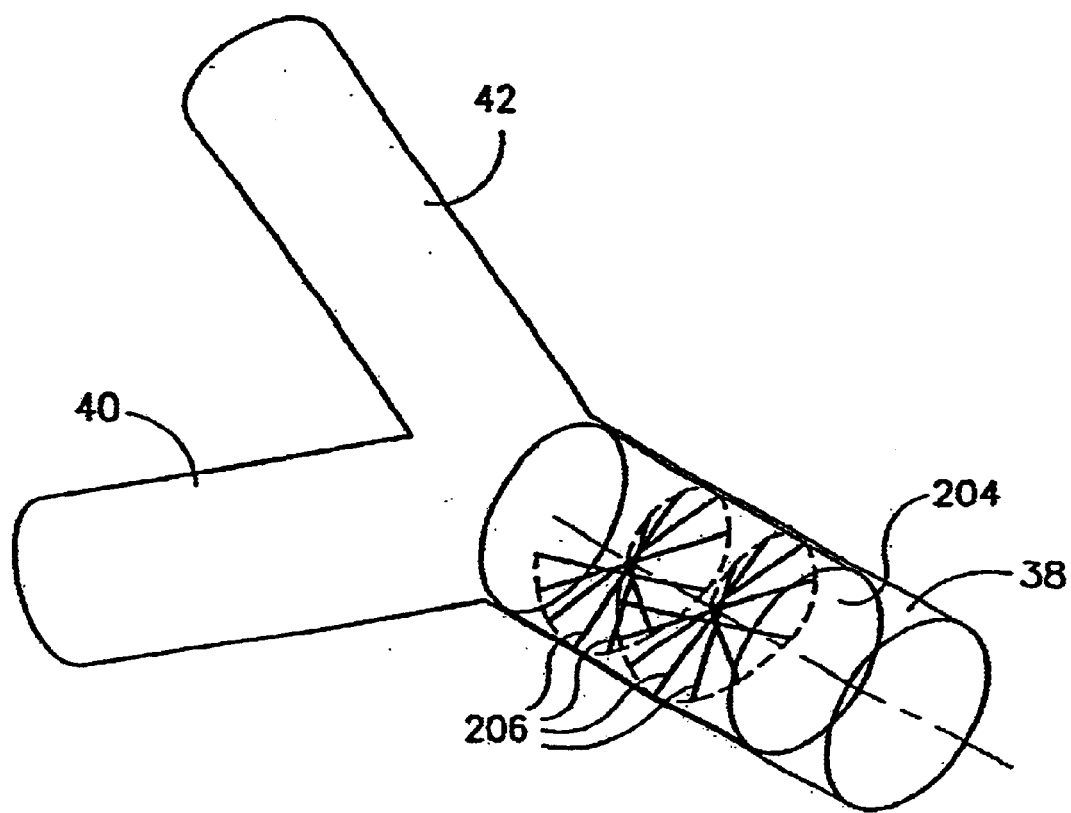
FIG. 3A is a schematic, isometric illustration of a deflecting device in accordance with still another embodiment located within the common carotid artery.
Figure 3B:
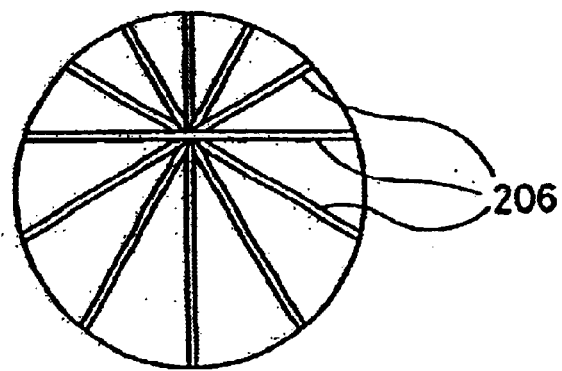
FIG. 3B is a cross-sectional view into the common carotid artery of the deflecting member.

In FIG. 3A, there is illustrated still another embodiment of a deflect device 204 received and anchored within the CCA 38. The device 204 comprises a helical structure of fine wires 206 which have a theoretical point of insertion shifted from the longitudinal axis of the artery 38. This can be understood from FIG. 3B which is a view through the CCA 38.

Figure 4A:
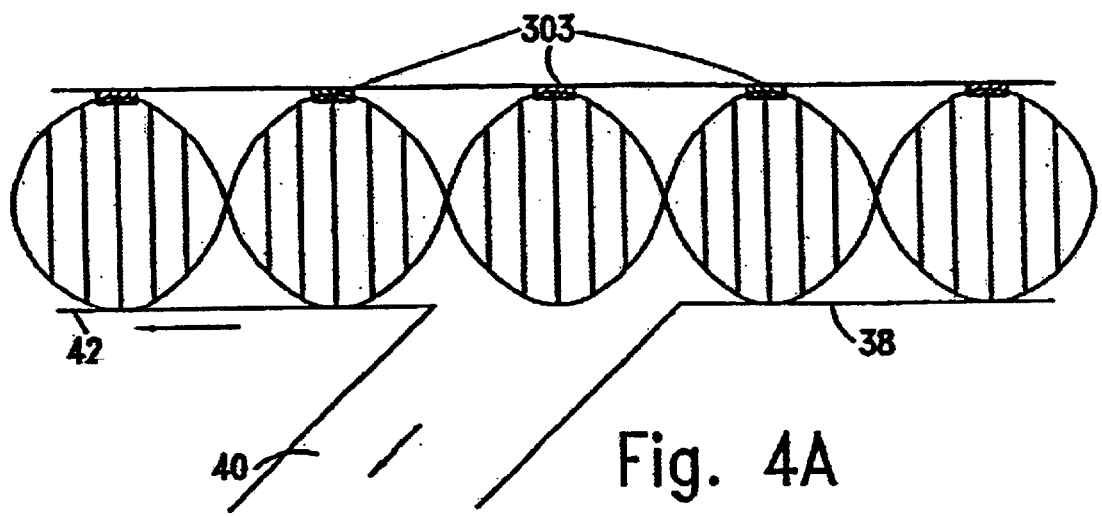
FIG. 4A is a schematic cross-section of a preferred embodiment of the device of FIG. 3.
Figure 4B:
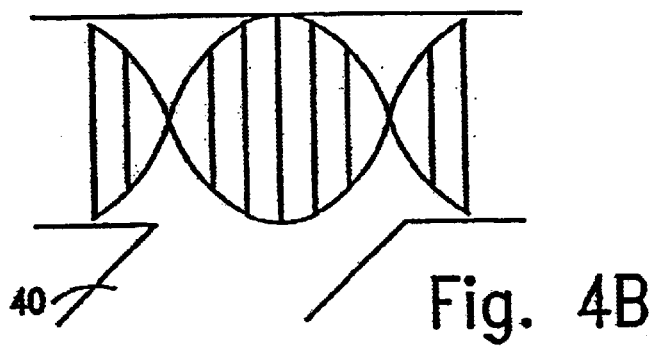
FIG. 4B shows the positioned relationship of the device of FIG. 4A and the ECA.

The arrangement is such that a helical movement is imparted to the embolic material flowing through the CCA 38, which is thus deflected into the ECA 42. This is further illustrated in FIG. 4. FIG. 4A shows in cross-sectional view of the helical deflecting element is positioned within the vessel. As seen in FIG. 4B, it is desirable to have the whole length of the helix last essentially the whole diameter of the ICA, to ensure that embolic material is deflected away from the opening.

Figure 4C:
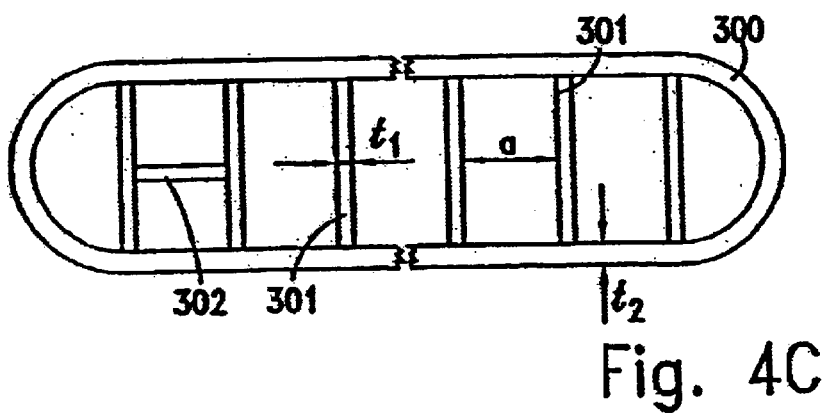
FIG. 4C schematically shows the frame of which the deflecting member of FIG. 4B is made.
Figure 4D:
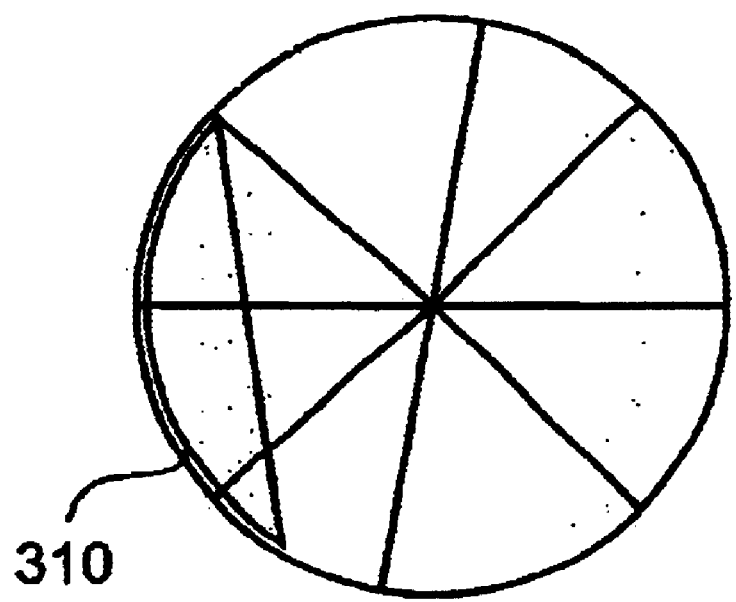
FIG. 4D is a cross-sectional view of the deflecting element of FIG. 4B along the axis of the artery.

The construction of the helical device of the preferred embodiment of FIG. 4A can be as in FIG. 4C, in which a frame 300 is equipped with struts (stages) 301, to form a ladder-like structure. The number of struts 301 may vary, according to the desired dimensions of the device. Intermediate strengthening elements 302 can be inserted, for strength reasons, between any pair of struts 301. Furthermore, more than one strengthening element can be provided between a pair of struts, and some or all pairs may be without any strengthening element, the number and nature of said strengthening elements being dictated solely by mechanical considerations. The frame 300 can be constructed so as to be "normally helical", viz., such that its normal configuration is that of FIG. 4A, and that a force must be exerted on it to bring it to the configuration of FIG. 4C. In order to deliver it, the ladder-like element of FIG. 4C is allowed to coil itself from a distended position, onto a portion of the circumference of a cylindrical delivery device (not shown). Withdrawal of the delivery device causes the device to assume its normal, helical position. The device, when in place, look from an axial direction of the CCA as schematically shown in FIG. 4D. The arc-like structure 310 shown on the left side of FIG. 4D represents the beginning of said ladder-like elements, and is in contact with the endothelial surface of the vessel wall.

Typical illustrative and non-limitative dimensions for the device of FIG. 4C are:

a—distance between stages—400$\mu$;

$t_1$—thickness of the struts—10–50$\mu$;

$t_2$—frame thickness—200$\mu$;

The device of the invention can be constructed in a way very similar to cardiac stents, although the dimensions are different and, therefore, allow for greater constructive flexibility. However, the man of the art will easily recognize the materials and expandable shapes suitable to make the stent of the invention. For instance, the stent and the deflecting device can be made of a material selected from nitinol, polymeric material, stainless steel, etc., and having a configuration selected from zigzag shape and sinusoidal shape. The filtering means of the deflecting device, if used, should have the following dimensions, in order to effectively prevent the entrance of at least a major part of dangerous embolic material: >200–400 $\mu$m. The diameter of the stent may somewhat vary for different individuals. However, the diameter in the closed state is Up to about 3 mm, while when expanded, the diameter may vary in the range of 5 mm to 10 mm. The diameter of the wire which makes up the body (or anchoring portion) of the device is preferably in the range 100 $\mu$m to 200 $\mu$m, while that of the wire used for the filtering device is preferably in the range of 10 $\mu$m to 200 $\mu$m. Of course, the entire device can also be constructed using the same dimensions, so that there is no difference in mesh size between the body of the device and its deflecting portion.

Any suitable method can be used to manufacture the device of the invention, such as laser cutting or chemical etching. These methods are conventional and well known to the skilled person, and are therefore not discussed herein in detail, for the sake of brevity. Additionally, markers can of course be provided, which are visible by any suitable technique, e.g., X-ray, to enable to impart to the stent the desired spatial position, such as marker 303 in FIG. 4A.

The device of the invention must fulfill certain predetermined conditions that will be detailed hereinafter. The skilled person will of course be able to devise various devices, of different shapes and properties, which fulfill said conditions. When testing a device of the invention under physiological conditions, namely:

$Re_{av}$=200–500

BPM (beats per minute)=40–180

Womersley=2–7 wherein $Re_{av}$ is the average Reynolds number, and Womersley is the dimensionless beat parameter;

the following conditions should preferably be met by the device of the invention:

1) $Re_{prox}$ between 0 and 4, preferably 1 or less (creeping or Stokes' flow)

2) 100 dyne/cm$^2$>Shear Stress>2 dyne/cm$^2$

3) The generation of thrombin should not exceed 40 nmole/minute, as measured according to the thrombin acetylation test.

wherein $Re_{prox}$ is the Reynolds number for the wire of which the deflect element is made, and the shear stress is measured at the device. As will be appreciated by the skilled person, the smaller the $Re_{prox}$ number the better. However, devices attaining larger $Re_{prox}$ numbers than indicated above may also be provided, and the invention is by no means limited to any specific $Re_{prox}$ number.

While some preferred embodiments of the invention have been illustrated and described in the specification, it will be understood by a skilled artisan that it is not intended thereby to limit the disclosure of the invention in any way, but rather it is intended to cover all modifications and arrangements falling within the scope and the spirit of the present invention. For example, the deflecting device may be a permanent device or may be removed from the vicinity of the carotid arteries at need Furthermore, the deflecting member may be integrally formed with, or detachably connected to, the anchoring member, wherein in some instances it might be necessary first to position the anchoring member and then to attach the deflecting member. Additionally, the deflecting member may be of different size, shape and pattern, depending on flow parameters and patient specific requirements.

What is claimed is:

1. An implantable device for implanting in the vicinity of the bifurcation of the common carotid artery of a subject into the internal carotid artery and the external carotid artery, to reduce the danger of a stroke, characterized in that said implantable device is configured and dimensioned to define, when the implantable device is implanted in the common carotid artery, a deflector extending radially inwardly into the common carotid artery and effective to deflect embolic material in the blood flowing through the common carotid artery into the external carotid artery to a greater extent than into the internal carotid artery, wherein:

the implantable device is comprised of a helical structure and is dimensioned to extend also into the external carotid artery and across the internal carotid artery opening; and wherein the implantable device includes an elongated frame of a ladder-type construction, including a pair of opposed, parallel long sides joined by a plurality of spaced struts spaced along the length of the long sides; said pair of long sides are twisted and connected one to another to form a curved end so as to anchor the implantable device in place within the common carotid artery and external carotid artery; said plurality of spaced struts defining a plurality of deflector elements effective to deflect embolic material in the blood flowing through the common carotid artery into the external carotid artery to a greater extent than into the internal carotid artery.

2. The implantable device according to claim 1, wherein said implantable device further includes at least one strengthening element joining two of said struts.

3. The implantable device according to claim 1, wherein the thickness of said long sides is greater than the thickness of said struts.

4. The implantable device according to claim 1, wherein at least one of said deflector elements comprise a plurality of wires arranged along a helical path within the common carotid artery and having an imaginary point of intersection which is offset with respect to a longitudinal axis of the common carotid artery.

5. The implantable device according to claim 4, wherein said deflector elements generate a centrifugal flow pattern effective to deflect embolic material in the blood flowing through the common carotid artery into the external carotid artery to a greater extent than into the internal carotid artery.

* * * * *